United States Patent [19]

Bertram et al.

[11] Patent Number: 6,072,077

[45] Date of Patent: Jun. 6, 2000

[54] 5-Z-OCTENYL ESTERS, PROCESS FOR THEIR PREPARATION AND THEIR USE

[75] Inventors: Heinz-Jürgen Bertram, Teterboro, N.J.; Matthias Güntert, Holzminden; Günter Kindel, Höxter, both of Germany

[73] Assignee: Haarmann & Reimer, GmbH, Holzminden, Germany

[21] Appl. No.: 08/870,114

[22] Filed: Jun. 5, 1997

[30] Foreign Application Priority Data

Jun. 5, 1996 [DE] Germany ............... 196 22 570

[51] Int. Cl.⁷ ............... C07C 69/02; C07C 67/08
[52] U.S. Cl. ............... 560/231; 560/238; 560/239
[58] Field of Search ............... 560/231, 238, 560/239

[56] References Cited

U.S. PATENT DOCUMENTS 4,658,071  4/1987  Seufert et al. ............... 568/903

FOREIGN PATENT DOCUMENTS 7970208  6/1979  Japan ............... C07C 33/02
556144  11/1974  Switzerland ............... A23L 1/26

OTHER PUBLICATIONS

Shiota, New Esteric Compounds . . . (Musa sapientum L.), J. Agric. Food Chem., 41, pp. 2056–2062, No Month Provided 1993.

H. Shiota, New Esteric Components in the Volatiles of Banana Fruit (Musa sapientum L.), J. Agric. Food Chem., vol. 41, No. 11, pp. 2056–2062, No Month Provided.

Organikum, pp. 402–407, 18$^{th}$ Edition, No Month Provided 1990.

L.F. Tietze, et al., Reakitonen und Synthesen, pp. 128–135, No Month Provided 1991.

R.G. Berger, et al., Geruchsaktive Spurenkomponenten des Bananenaromas, Chem. Mikrobiol. Technol. Lebensm., 10, pp. 120–124, No Month Provided (1986).

*Primary Examiner*—Johann Richter
*Assistant Examiner*—Rosalynd Keys
*Attorney, Agent, or Firm*—Norris, McLaughlin & Marcus, P.A.

[57] ABSTRACT

5-Z-octenyl esters of the formula

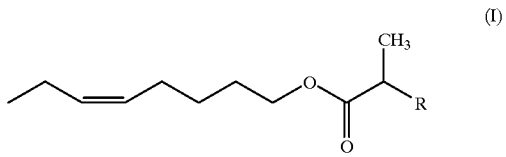

in which
R represents hydrogen, methyl or ethyl, have an intensive mango aroma, so that the compounds I can be added to fruit compositions and aroma compositions; they have flavor-intensifying and flavor-rounding action.

3 Claims, No Drawings

5-Z-OCTENYL ESTERS, PROCESS FOR THEIR PREPARATION AND THEIR USE

The invention relates to novel 5-Z-octenyl esters, a process for their preparation and their use as aroma substances.

It has been found that the 5-Z-octenyl esters of selected carboxylic acids have valuable organoleptic properties.

The invention relates to compounds of the formula

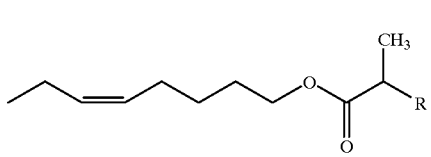

in which

R represents hydrogen, methyl or ethyl.

The compounds I can be prepared by esterification of 5-Z-octenol with carboxylic acids, acyl halides or carboxylic anhydrides.

The invention therefore further relates to a process for the preparation of the compounds I by esterification of 5-Z-octen-1-ol with a compound of the formula

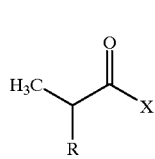

in which

X represents hydrogen, chlorine, bromine or iodine, or with a compound of the formula

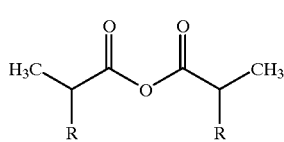

where R in each case has the meaning specified above.

The general reaction conditions for esterifications of alcohols with acids are known (Organikum [Organic Chemistry], 18th edition, Deutscher Verlag der Wissenschaften, Berlin 1990; L. F. Tietze, Th. Eicher: Reaktionen und Synthesen [Reactions and Syntheses], G. Thieme Verlag, Stuttgart, New York 1991).

The esterification can be carried out at temperatures from 0° C. to 200° C., preferably from 20° C. to 150° C., optionally in inert solvents such as ethers, preferably methyl tert-butyl ether or tetrahydrofuran, in aromatic and (cyclo) aliphatic hydrocarbons, preferably toluene, xylene, n-hexane n-heptane, cyclohexane, methylcyclohexane or decalin or in esters, preferably ethyl acetate, propyl acetate, butyl acetate, methyl propionate, ethyl propionate, propyl propionate or butyl propionate, at atmospheric pressure or under pressure, in the presence or absence of bases or acids.

The compounds (I) of the invention are valuable aroma substances; they are distinguished by an intensive mango aroma. This is all the more surprising, since the previously known 5-Z-octenyl esters lack the typical, intensive mango aroma.

Thus, for example, 5-Z-octenyl acetate, 3-methylbutyrate and pentanoate have a typical banana aroma (R. G. Berger, F. Drawert, H. Kollmannsberger, Chem. Mikrobiol., Technol. Lebensm. (1986) 10, 120–4; H. Shiota, J. Agric. Food Chem. 41, (1993) 2056 JPN Kokai Tokkyo Koho 7970, 208 (1979).

The flavour descriptions determined for the individual compounds (I) of the invention in 0.5% strength by weight aqueous sodium chloride solution by a test panel of 6 specially trained testers are as follows:

5-Z-Octenyl propionate:
  at an addition of 7.5 ppm: melon, mango, cucumber, fatty
5-Z-Octenyl isobutyrate:
  at an addition of 7.5 ppm: mango, green, melon
5-Z-Octenyl 2-methylbutyrate:
  at an addition of 7.5 ppm: melon, full-bodiedness, soft, cucumber With their specific mango aroma, the compounds (I) of the invention have flavour-intensifying and flavour-rounding action in fruit compositions and aroma compositions.

The aroma compositions prepared using the compounds of the invention can be used in the entire food and drinks sector. They are suitable, in particular, for fat compositions, bakery products, fruit preparations, juice concentrates, icecream and fruit preserves.

The 5-Z-octenyl esters of the invention are preferably used in amounts of 1 ppm to 1% by weight, in particular 5 ppm to 500 ppm, based on the ready-to-eat food.

The percentages used in the examples are by weight.

EXAMPLES

Example 1

5-Z-Octenyl propionate 5 g of 5-Z-octenol, 5.3 g of dimethylbeneylamine and 0.1 g of dimethylaminopyridine are placed into 50 ml of diethyl ether at 0° C. At this temperature, 4.0 g of propionyl chloride are then added dropwise in the course of 30 minutes. After addition is complete, the mixture is further stirred for 16 hours at room temperature. For work-up, the mixture is poured into dilute sulphuric acid, washed once with ether, and the combined organic phases are washed twice with water, dried and concentrated. 6 g of crude product are obtained; after bulb tube distillation, 5.4 g of a product which has a purity according to GC of 95% are obtained.

IR spectrum (film):

Wave number [cm$^{-1}$]

| | |
|---|---|
| 807.6 | w |
| 1029.6 | w |
| 1087.4 | m |
| 1196.1 | s |
| 1352.4 | m |
| 1462.2 | w |
| 1736.1 | s |
| 2871.2 | m |
| 2960.1 | m |
| 3001.7 | m |

(Intensity of the IR bands: w = weak, m = medium, s = strong)

Examples 2 and 3

5-Z-Octenyl isobutyrate and 2-methylbutyrate

When isobutyryl chloride or 2-methylbutyryl chloride was used instead of propionyl chloride, 5-Z-octenyl isobutyrate or 5-Z-octenyl 2-methylbutyrate, respectively, was obtained.

IR spectrum (film):

| 5-Z-Octenyl isobutyrate | | 5-Z-Octenyl 2-methylbutyrate | |
|---|---|---|---|
| Wavenumber [cm$^{-1}$] | | | |
| 1162 | s | 1158.7 | m |
| 1199.6 | s | 1190.3 | m |
| 1346.8 | m | 1266.5 | w |
| 1389.2 | w | 1357.6 | w |
| 1467.2 | m | 1461.4 | m |
| 1731.8 | s | 1730.8 | s |
| 2872.1 | m | 2873.3 | m |
| 2938.6 | m | 2935.9 | m |
| 2963.9 | m | 2962.8 | s |
| 3004.7 | m | 3007.1 | m |

Use Example

| | Parts by weight |
|---|---|
| Dimethyl sulphide | 5 |
| Caryophyllene | 10 |
| α-Pinene | 30 |
| Nerol | 30 |
| 3-Z-Hexenyl acetate | 35 |
| Acetylmethylcarbinol | 50 |
| 2,5-Dimethyl-4-hydroxy-3(2H)-furanone | 60 |
| 3-Z-Hexenol | 100 |
| Hexanol | 110 |
| γ-Decalactone | 180 |
| Compound 1 | 10–100 |
| Propylene glycol | 290–380 |
| | 1000 |

What is claimed is:

1. Compounds of the formula

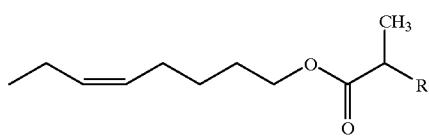

in which

R represents hydrogen, methyl or ethyl.

2. Process for the preparation of the compounds according to claim 1 by esterification of 5-Z-octen-1-ol with a compound of the formula

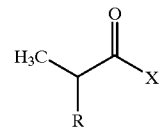

in which

X represents hydrogen, chlorine, bromine or iodine, or with a compound of the formula (III)

$$H_3C \overset{O}{\underset{R}{\diagdown}} O \overset{O}{\underset{R}{\diagup}} CH_3$$

where R in each case has the meaning specified in claim 1.

3. A method for intensifying mango flavor or aroma, rounding the mango flavor or aroma, or both, of foods or drinks, which comprises adding to said foods or drinks a compound according to claim 1.

* * * * *